United States Patent [19]

Seto et al.

[11] Patent Number: 4,615,839

[45] Date of Patent: Oct. 7, 1986

[54] METHOD OF PREPARING FATTY ACID COMPOSITION CONTAINING HIGH CONCENTRATION OF EICOSAPENTAENOIC ACID

[75] Inventors: Akira Seto; Shoko Yamashita, both of Yokohama, Japan

[73] Assignee: The Nisshin Oil Mills, Ltd., Japan

[21] Appl. No.: 681,025

[22] Filed: Dec. 13, 1984

[30] Foreign Application Priority Data

Dec. 21, 1983 [JP] Japan ................................. 58-239639

[51] Int. Cl.$^4$ ........................... C11B 1/10; C11B 3/00
[52] U.S. Cl. ................................. 260/412; 260/412.4; 260/420; 260/428.5
[58] Field of Search ..................... 260/420, 428.5, 412, 260/412.4

[56] References Cited

U.S. PATENT DOCUMENTS 4,377,526  3/1983  Fujita et al. ....................... 260/428.5

OTHER PUBLICATIONS (Abstract From Agricola: Bibliography of the Department of Agriculture) Ackman et al., *Journal of the Canadian Dietetic Association*, vol. 43(2), 1982, pp. 150–154.
Bligh, E. G. and Dyer, W. J., *Canadian Journal of Biochemistry and Physiology*, vol. 37, No. 8, pp. 911–917.
Christie, William, *Lipid Analysis*, Pergamon Press, NY, 1973, pp. 30–36, and pp. 176–178.
Gellerman et al., *Biochimica et Biophysica Acta*, 388 (1975), 277–290.
Biochemistry and Utilization of Marine Algae, Apr. 1983, published by Koseisha Koseikaku K.K., Japan, Table on p. 47.
Bulletin of the Japanese Society of Scientific Fisheries 1980, vol. 46, pp. 35–41.
Seiyaku Kojo, *Medicine Manufacturing Factory*, vol. 4, No. 12, 1984, pp. 861–863, "New Fat and Oil Components".

*Primary Examiner*—Charles F. Warren
*Assistant Examiner*—Elizabeth A. Flaherty
*Attorney, Agent, or Firm*—Bacon & Thomas

[57] ABSTRACT

A fatty acid composition is produced by subjecting a lipid composition extracted from marine chlorella to solvent fractionation to remove neutral fats, chlorophyll, sterols and majority of phospholipids, thereby providing a polar lipid composition. The polar lipid composition is then subjected to hydrolysis to liberate fatty acids. Finally, the fatty acids are recovered, thereby providing a fatty acid composition with not less than 60% by weight of eicosapentaenoic acid.

9 Claims, No Drawings

METHOD OF PREPARING FATTY ACID COMPOSITION CONTAINING HIGH CONCENTRATION OF EICOSAPENTAENOIC ACID

BACKGROUND OF THE INVENTION

1. Field of the Invention

The present invention relates to a process for preparing a mixture of fatty acids containing eicosapentaenoic acid and, more particularly, to a process for preparing a fatty acid mixture containing a high concentration of eicosapentaenoic acid from a lipid component extracted from marine chlorella.

2. Description of the Prior Art 5,8,11,14,17-Eicosapentaenoic acid (hereafter referred to as EPA) is a substance that has recently been recognized as an agent for preventing and curing cerebral thrombosis and arteriosclerosis. It is known that EPA is contained in fish oils and oils and fats of marine plants (algae). Nowadays, it is extracted and purified wholly from oils of fish such as sardines or the like. Among fish oils, the ones containing a high concentration of EPA contain EPA in an amount of approximately 20% by weight of the total fatty acids. For use as health food, a composition of fatty acids is used in which the concentration of EPA is increased to approximately 25 to 30%. For use as pharmaceuticals, a fatty acid composition containing higher than 90% of EPA has been prepared experimentally.

Since, however, fish oils contain a high concentration of highly unsaturated fatty acids (containing a number of carbon-carbon double bonds) such as docosahexaenoic acid and the like similar in nature and structure to EPA, it is not easy to increase the concentration of EPA in the fatty acid composition obtained from fish oils. Particularly, pharmaceuticals require a fatty acid mixture containing EPA in a concentration of 90% or more. In order to attain such a high EPA concentration, a complex combination of treatment procedures such as urea adduct process, solvent extraction, fractional distillation and column chromatography is required.

SUMMARY OF THE INVENTION

It is, therefore, an object of the present invention to provide a process that produces a composition of fatty acids with a high concentration or a high purity of EPA in a simple procedure.

In accordance with the present invention, a method of producing a fatty acid composition is provided which comprises the steps of:

subjecting a lipid composition extracted from marine chlorella to solvent fractionation to remove neutral fats, chlorophyll, sterols and phospholipids and thereby provide a polar lipid composition mainly comprising glycolipids and glyco-phospholipids, subjecting the polar lipid composition to hydrolysis to liberate fatty acids, and recovering the free fatty acids to provide a fatty acid composition containing EPA in a concentration of 60% by weight or more.

The thus prepared fatty acid composition may then be subjected to a urea adduct process, thereby yielding a fatty acid compositon containing EPA in a concentration as high as 90% by weight or more.

It is to be understood in this specification that a fatty acid referred to herein is meant to be an aliphatic monocarboxylic acid.

DETAILED DESCRIPTION OF THE PREFERRED EMBODIMENTS

As a result of research on processes capable of providing high purity EPA from a natural source, it was found by the present inventors that marine chlorella contain a high concentration of total lipids (ranging from approximately 30 to 40% by weight) and a high concentration of EPA in the total fatty acids (ranging from approximately 35 to 45% by weight) as well as a low concentration of highly unsaturated fatty acids other than EPA in the total lipids. It was further found that the marine chlorella is easily cultured. From these findings, they have developed a process for producing high purity EPA from marine chlorella.

The marine chlorella used in the present invention is a monocellular green algae that is very well known in the art. The source of the marine chlorella does not matter. Natural marine chlorella may be employed, however, when a large amount is needed, it is preferable to culture the marine chlorella. The culturing of chlorella is relatively easy, and chlorella is generally cultured, for instance, as food for Rotifer. Culturing may be done under the atmospher using a pool with a depth of about 50 cm which is filled with natural seawater as a culture medium in which minute amounts of nitrogen, phosphorus and potassium sources have been added. Although incubation temperatures and incubation periods may vary widely with season and place, in Japan the culture is usually carried out in spring and autumn.

Lipids may be extracted from marine chlorella by conventional procedures. The extraction may be carried out with a mixture of a non-polar and polar organic solvents. The non-polar solvent may include, for example, hexane, chloroform, ether or a mixture thereof, and the polar solvent may include, for instance, a lower alcohol such as ethanol, methanol, isopropanol, or a mixture thereof. Usually, the non-polar and the polar solvents are mixed in a ratio of the former to the latter ranging from approximately 2:1 to 1:1 by volume. The extraction may be carried out at a temperature ranging from room temperature to 60° C. by using from 5 to 20 parts by volume of the mixed solvent per part by volume of powdered dry marine chlorella. Although there is no limit, the extraction period usually ranges from 30 minutes to 3 hours. To carry out the extraction in large quantities, an extraction tank with a refluxing apparatus, equipped with a cell homogenizing apparatus such as polytron homogenizer, may be employed. After the extraction, the solvent may be removed by distillation under reduced pressure at temperatures ranging from approximately 40° to 60° C. to provide a lipid composition that contains triglycerides, phospholipids, glycolipids, glyco-phospholipids, chlorophyll, beta-carotene, sterols and the like.

The thus prepared lipid composition is then subjected to solvent fractionation. This process allows the lipid composition to adequately contact the non-polar organic solvent mentioned above or a mixture thereof, thereby permitting the neutral fatts, sterols and chlorophyll to transfer to the solvent and thus be removed. This extraction may generally be carried out with a solvent at a rate ranging from 5 to 20 parts by weight per part by weight of the lipid composition at temperatures from approximately 20° to 40° C. for approximately 30 minutes to 1 hour. After the extraction, the solvent phase is removed by filtration, and the residue is then brought into contact with acetone, usually at a temperature of approximately 4° C., and is left overnight. The amount of acetone used may range from approximately 10 to 20 parts by weight per part by weight of the residue. The extraction with acetone prevents almost all of the phospholipids contained in the lipid composition from dissolving in the acetone. The acetone phase is then collected, and the solvent, acetone, is removed by distillation under reduced pressure, thereby providing a fraction of polar lipids containing nearly no phospholipids and consisting substantially of glycolipids and glyco-phospholipids. Generally, the yield of the polar lipid fraction is approximately 10 to 30% by weight with respect to the weight of the lipid composition as extracted from the marine chlorella.

The polar lipid fraction is then subjected to hydrolysis which is usually carried out in an appropriate organic solvent such as an alcohol, e.g., methanol, with the aid of an acid such as a mineral acid, e.g., hydrochloric acid or sulfuric acid, or an alkali such as sodium hydroxide or potassium hydroxide, which is approximately 0.3 parts by weight or more per part by weight of the polar lipid fraction. The temperature for hydrolysis may range from 70° to 80° C., and the hydrolysis time from 15 minutes to 2 hours. The hydrolysis allows the glycolipids and the glyo-phospholipids in the polar lipid fraction to be decomposed and consequently liberate fatty acids. If phospholipids remain in the polar lipid fraction, they will be decomposed, too. After unsaponified materials are extracted and removed with a nonpolar solvent such as petroleum ether under an alkali condition, the residue is acidified and the fatty acids are further extracted with an organic solvent such as petroleum ether. The extraction of the fatty acids is preferably carried out at temperatures ranging from 20° to 40° C. After the extraction, the removal of the solvent yields a desired fatty acid composition.

The resulting fatty acid composition contains 60% by weight or more of EPA. The other fatty acid components of the fatty acid composition may include palmitic acid, palmitoleic acid and arachidonic acid as major components as well as oleic acid, myristic acid, tetradecenoic acid, lauric acid and dodecenoic acid as other components.

Among the above-mentioned components contained in the fatty acid composition, saturated fatty acids and fatty acids having one double bond, particularly palmitic acid and palmitoleic acid, may be completely removed by the urea adduct process. This process may be conducted by using urea in the amount of approximately 2 to 3 parts by weight and methanol in the amount of approximately 10 to 15 parts by weight at temperatures of approximately 60° C. for 1 to 2 hours. After the reaction, the reaction mixture is left to stand overnight at temperatures as low as −20° C. to +4° C. The materials undissolved in methanol are then removed by filtration or the like, and methanol is distilled off from the methanol solution. The residue is then treated with an aqueous hydrochloric acid solution to decompose urea and then washed with warm water. After the water is removed, the residue is subjected to extraction with a polar solvent such as ether. The removal of the solvent from the solvent phase yields a fatty acid composition containing EPA in the amount of 90% by weight or more. The resulting fatty acid composition may be used as reagents and as raw pharmaceutical materials.

The present invention will be described in more detail by way of working examples.

EXAMPLE 1

A mixture of chloroform with methanol in a ratio of the former to the latter of 2 to 1 (volume/volume) was added to approximately 100 grams of dry cells obtained by incubating *Chlorella minutissima* in a seawater medium, in a volume proportion of 10 times the dry cells. The mixture was treated in a polytron homogenizer at a temperature of 60° C. for 1 hour to extract lipids while destroying the cells. After the content was filtered, the solvent was removed by distillation from the filtrate under reduced pressure to yield a lipid composition.

One kilogram of a mixture of solvents, hexane and ether at the ratio of 1/1 (volume/volume), were added to 100 grams of the resulting lipid composition, and the mixture was stirred at 20° C. for 1 hour. After the mixture was filtered, the residue was mixed with 1 kilogram of acetone and was allowed to stand at 4° C. for 12 hours. The resulting acetone phase was collected, and the acetone was distilled off under reduced pressure to yield a polar lipid composition.

A mixture of 2N sodium hydroxide aqueous solution with methanol in the ratio of the former to the latter of 1 to 9 (volume/volume) was added to approximately 3 grams of the polar lipid composition, and the mixture was subjected to hydrolysis under nitrogen streams at 80° C. for 2 hours. After the unsaponified materials were removed with petroleum ether, the remaining portion was rendered acidic using hydrochloric acid, and extraction with petroleum ether was performed. The removal of the petroleum ether from the resulting petroleum ether phase gave 2 grams of a desired fatty acid composition. The analysis by means of gas chromatography of the resulting fatty acid composition yielded the components shown in Table 1 below:

TABLE 1

| Fatty acid | (1) 16:0 | (2) 16:1 | (3) 18:0 | (4) 18:1 | (5) 18:2 | (6) 20:4 | (7) 20:5 | Others |
|---|---|---|---|---|---|---|---|---|
| % by weight | 7.0 | 7.0 | 0 | 0.3 | 0 | 4.6 | 69.5 | 11.6 |

Notes:
(1) Palmitic acid
(2) Palmitoleic acid
(3) Stearic acid
(4) Oleic acid
(5) Linoleic acid
(6) Arachidonic acid
(7) EPA

EXAMPLE 2

One gram of the fatty acid composition obtained in Example 1 was dissolved in 6 grams of methanol, and the solution was mixed with 0.8 gram of urea. After the mixture was allowed to react at 60° C. for 2 hours, the reaction mixture was cooled gradually to room temperature and allowed to stand for 1 hour at the same temperature and then at −20° C. overnight. After the mixture was filtered, the methanol was removed from the filtrate by distillation leaving the residue which in turn was washed twice with a five-fold amount of warm water containing a 0.7% by weight 6N hydrochloric acid and thereafter 4 to 5 times with warm water. After drying the resulting residue, it was treated with 2-fold amount of ether, and the ethereal phase was collected.

The removal of the ether from the ethereal phase yielded a desired fatty acid composition. The composition was analyzed as in Example 1, and the components are shown in Table 2 below.

TABLE 2

| Fatty acid | 16:0 | 16:1 | 18:0 | 18:1 | 18:2 | 20:4 | 20:5 | Others |
|---|---|---|---|---|---|---|---|---|
| % by weight | 0 | 0 | 0 | 0 | 0 | 5.9 | 93.0 | 1.1 |

As described above, the present invention allows high purity EPA to be produced from marine chlorella with a simple procedure.

What is claimed is:

1. A method of producing a fatty acid composition comprising the steps of:
   extracting a lipid composition from marine chlorella;
   subjecting said lipid composition to solvent fractionation to remove neutral fats, chlorophyll, sterols and majority of phospholipids, thereby providing a polar lipid composition;
   subjecting the polar lipid composition to hydrolysis to liberate fatty acids; and
   recovering the fatty acids, thereby providing a fatty acid composition with not less than 60% by weight of eicosapentaenoic acid.

2. A method according to claim 1, wherein the solvent fractionation comprises transferring the neutral fats, sterols and chlorophyll contained in the lipid composition to a non-polar organic solvent by bringing the lipid composition into contact with the non-polar organic solvent, removing the organic solvent phase, bringing the resulting residue into contact with acetone to separate materials dissolvable in acetone, and removing acetone from the acetone-soluble materials to yield the polar composition as a residue.

3. A method according to claim 1, wherein the hydrolysis comprises bringing the polar lipid composition into contact with an acid or an alkali.

4. A method according to claim 3, wherein the acid or alkali is added at a ratio of not less than 0.3 part by weight with respect to one part by weight of the polar lipid composition.

5. A method according to claim 4, wherein the hydrolysis is carried out at a temperature of approximately 70° C. to 80° C. for approximately 15 minutes to 2 hours.

6. A method according to claim 1, further comprising the step of subjecting the fatty acid composition to a urea adduct process to remove a saturated fatty acid component and an unsaturated fatty acid component having one double bond contained in the fatty acid composition, thereby providing a fatty acid composition with high purity containing not less than 90% by weight of eicosapentaenoic acid.

7. A method according to claim 6, wherein the urea adduct process comprises reacting the fatty acid composition with urea in a solvent, collecting the resulting solvent phase after allowing the reaction mixture to stand at a low temperature, removing the solvent from the solvent phase, and decomposing the remaining urea by treating the residue with hydrochloric acid.

8. A method according to claim 7, wherein the urea is added at a ratio ranging from 2 to 3 parts by weight with respect to one part by weight of the fatty acid composition.

9. A method accoding to claim 7, wherein the solvent is methanol.

* * * * *